United States Patent [19]

Crews et al.

[11] 4,299,726
[45] Nov. 10, 1981

[54] PROCESS FOR PREPARING WHOLE BLOOD REFERENCE CONTROLS HAVING LONG TERM STABILITY, PRECONDITIONING DILUENT AND MEDIA THEREFOR

[75] Inventors: Harold R. Crews, Miami; David L. Chastain, Jr., Fort Lauderdale; Stephen L. Ledis, Hialeah, all of Fla.

[73] Assignee: Coulter Electronics, Inc., Hialeah, Fla.

[21] Appl. No.: 36,794

[22] Filed: May 7, 1979

[51] Int. Cl.³ .................. G01N 33/48; C09K 3/00
[52] U.S. Cl. .................. 252/408; 23/230 B; 424/2; 424/3; 424/101; 435/4
[58] Field of Search .................. 252/408; 23/230 B; 424/2, 3, 101; 435/4

[56] References Cited

U.S. PATENT DOCUMENTS

| | | | |
|---|---|---|---|
| 3,574,137 | 4/1971 | Decasperis | 252/408 |
| 3,873,467 | 3/1975 | Hunt | 252/408 |
| 3,956,477 | 5/1976 | Price et al. | 424/12 |
| 3,962,125 | 6/1976 | Armstrong | 252/408 |
| 3,973,913 | 8/1976 | Louderback | 252/408 |
| 3,977,995 | 8/1976 | Louderback et al. | 252/408 |
| 4,102,810 | 7/1978 | Armstrong | 252/408 |
| 4,213,876 | 7/1980 | Crews et al. | 252/408 |

OTHER PUBLICATIONS

Billington, David., et al.; Biochim. Biophys. Acta., vol. 509, pp. 33–47, (1978).
Coleman, R., et al.; Biochim. Biophys. Acta., vol. 426, pp. 776–780, (1976).
Seeman, P., et al.; Biochem. Pharmacology, vol. 15, pp. 1737–1752, (1966).
Seeman, P.; Biochem. Pharmacology, vol. 15, pp. 1753–1766, (1966).
Premachamdra, B. R., et al.; Biochim. Biophys. Acta., vol. 550, pp. 245–258, (1979).
Ohki, S., et al.; Biochim. Biophys. Acta., vol. 507, pp. 395–407, (1978).
Fischer, H., et al.; Proc. 10th Congr. Int. Soc. Blood Transf., Stockholm 1964, pp. 616–626, (1965).
Akerblom, O., et al.; Transfusion, vol. 7, No. 1, pp. 1–9, (Jan.–Feb. 1967).
Dern, R. J., et al.; J. Lab. Clin. Med., vol. 69, No. 6, pp. 968–978, (Jun. 1967).
Nakao, M., et al.; Nature, vol. 187, pp. 945–946, (Sep. 1960).
Nakao, M., et al.; Nature, vol. 197, pp. 877–878, (Jun. 2, 1962).

*Primary Examiner*—Teddy S. Gron
*Attorney, Agent, or Firm*—Meredith P. Sparks; Gerald R. Hibnick

[57] ABSTRACT

A process for preparing whole blood reference controls having long term stability up to six months for devices using electronic means for whole blood determinations including platelet count and mean cell volume and red blood distribution width. The preconditioning diluent for the red blood cells consists essentially of an aqueous solution of lactose, sodium azide, and a non-ionic surfactant and is pH buffered and osmolality adjusted. The media of the whole blood control includes lactose, fungicides and antibiotics, and supplementary agents including purine nucleosides. It also includes additional components which alter red blood cell membranes including bile salts and cholic acid derivatives, phenothiazine compounds and the salts thereof having antihistamine properties, and 4-aminobenzoic acid ester derivatives and their salts having local anesthetic properties. In the process, the red blood cells are separated from the whole blood and preconditioned by the diluent to attain desired size distribution width and volume. The preconditioned red blood cells then are mixed in the media in suitable number for yielding the desired cell count for the whole blood reference control.

14 Claims, No Drawings

PROCESS FOR PREPARING WHOLE BLOOD REFERENCE CONTROLS HAVING LONG TERM STABILITY, PRECONDITIONING DILUENT AND MEDIA THEREFOR

BACKGROUND OF INVENTION

This invention relates to a process for preparing whole blood reference controls having long term stability for devices using electronic means for whole blood determinations, and media therefor.

The importance of a quality control system in the Clinical Hematology Laboratory has been widely emphasized. Especially important is the inclusion of reference blood cell controls which monitor the accuracy and precision of electronic blood cell counting devices. In the past, artificial latex particles and erythrocytes, prepared in fixatives such as glutaraldehyde and formalin, have been used as standard suspensions. These preparations have a number of disadvantages: (1) distortion of shape and volume of the red blood cells; (2) increased viscosity of the suspending media; (3) agglutination of the fixed erythrocytes; (4) inability to perform simultaneous erythrocyte counts and hemoglobin determinations. Several commercial companies have marketed modified whole blood controls for use in monitoring electronic counters, but it is well recognized that there is need for improved stability of reference control material for maintaining the accuracy of red cell counts and other parameters when employing electronic counting methods.

Electronic counters which employ the Coulter principle first described in U.S. Pat. No. 2,656,508 express a true reflection of particle counts. Whole blood reference controls should approximate that of fresh whole blood as closely as possible. Attempts have been made to provide suitably sized particles in stable suspensions by the use of ragweed pollen, polystyrene, latex, various organic materials and tanned red cells. None of these suspensions have proved suitable for use as a standard for red cell counting.

U.S. Pat. No. 3,549,994 to Coulter Electronics, Inc. of Hialeah, Florida describes the Coulter Counter ® Model S, which is a semi-automated analytical instrument that measures seven blood parameters simultaneously; i.e., white blood cell (WBC) count, red blood cell (RBC) count, hemoglobin (Hb), Hematocrit (HCT), mean cell volume (MCV), mean cell hemoglobin (MCH), and mean cell hemaglobin concentration (MCHC). Values for the (WBC), (RBC), (Hb), and (MCV) are obtained from direct readings while the (HCT), (MCH), and (MCHC) are computed electronically. The measurement of these seven parameters can be accomplished either on whole blood or on capillary blood. Approximately one milliliter (ml) of whole blood is aspirated (utilized) for the macro measurement; whereas, 44.7 microliters of capillary blood diluted in 10 ml of an isotonic balanced saline solution, or other suitable diluent is used for the micro measurement.

Quality control of the Coulter Counter ® Model S is accomplished with the Coulter Counter ® cell control 4C ®, which is a modified whole blood hematology reference control prepared from fresh human blood. It is stable for about 30 days at 2° C. to 8° C., and it is stable for five hours at room temperature before the mean cell volume (MCV) is affected. Cell control 4C ® is not used as a calibration standard. Many workers have used fresh blood from normal persons to calibrate the Coulter Counter ® Model S. Other suitable whole blood reference controls might also be used.

A variety of standard suspensions have been used also to monitor cell counts. One major disadvantage of these suspensions is that, individually, they do not simulate a whole blood sample. For instance, none provide the necessary components for the simultaneous measurements of the seven blood parameters mentioned previously.

The specific parameters of the red blood cells which it is desirable to measure dictate the necessary characteristics of a suitable media for a whole blood reference control. It is desirable to know the volume of the red cell. Once this measurement is ascertained and the red cells have been counted, the packed cell volume or hematocrit (HCT) can be computed. The reference control media also should be capable of equilibrating and stabilizing the volume of red blood cells in the sample so that its cubic volume can be measured (MCV).

The media must be capable of maintaining the chemical and physical integrity of the red blood cells prior to and during the procedure. The blood cells are required to retain the same physical character in the media as exhibited initially. An additional parameter, the red blood cell distribution width (RDW), requires stability of the distribution of the red blood cells. For this purpose the media must be isotonic relative to the solutions in the blood cells.

The Coulter Counter ® Model S Plus, which is capable of electronic sizing and counting of whole blood human platelets which are only ½ to ⅓ the diameter of erythrocytes, requires a control such as cell control 4C ®, and in addition it requires a control for platelets or materials that simulate human platelets in size and distribution. This has presented a problem in that any particulate matter present in the volume size and distribution range of human platelets will give erroneous results because the presence of foreign particles will result in the enumeration thereof as a blood cell or constituent. High background counts contributed by excess debris cannot be tolerated. Therefore, it is required that the whole blood reference control be rendered free of any particulate matter that would perhaps demonstrate interference in lower size thresholds corresponding to that of human platelet size and distribution. Concomitantly, the media must be bacteriostatic in nature so as to prevent the growth of microorganisms after packaging the media.

New diagnostic parameters utilizing electronic counting devices have made it necessary to find a more stable whole blood reference control. One such parameter is the measurement of red cell distribution width. Normally, under certain defined conditions, such as when fixatives (glutaraldehyde-formaldehyde suspensions) are employed, desired stable red cell distributions are maintained. However, these preparations have a number of disadvantages.

SUMMARY OF THE INVENTION

This invention relates to a process for preparing a whole blood reference control for devices using electronic means for whole blood determinations, and especially for determining parameters which include platelet count, mean cell volume and red blood cell distribution width. The process includes use of a preconditioning diluent, which relatively quickly reduces the volume of the red blood cells, stabilizes their size distribution width, and has other attributes. The media of this whole blood reference control is substantially free from particulate matter in the lower size thresholds corresponding to that of human platelet size. The media has long term stability for use up to 6 months. The media includes lactose, one or more fungicides and antibiotics, and agents including purine nucleotides or nucleosides such as 5'-AMP, adenine and inosine. Also, ingredients are added that alter the red blood cell membrane. These include bile derivations such as cholic acid, deoxycholic acid, and the like, phenothiazine compounds, and the salts thereof, having antihistamine properties such as phenergan, and 4-aminobenzoic acid ester derivatives and their salts which are local anesthetics such as procaine.

DETAILED DESCRIPTION OF THE INVENTION

According to the process of this invention whole human or animal blood first is centrifuged to obtain packed red cells, and then the packed red cells are resuspended in a preconditioning diluent, which reduces their volume and stabilizes the cells, size distribution width, in preparation to the treating by the media. A preferred formulation for the preconditioning diluent is the following:

|  | One Liter: | Approximate Amounts: |
|---|---|---|
| Lactose | 90.0 g | 25–100 gms/L |
| Sodium azide | 1.5 g | 0.5–4.0 gms/L |
| Trisodium citrate dihydrate | 5.0 g | 2.5–5.0 gms/L |
| Citric acid monohydrate | 0.1 g | 0.05–0.2 gms/L |
| Non-ionic surfactant (Pluronic F68) | 1.0 g | 0.25–1.5 gms/L |
| Water | QS to 350 mOs/kg | |
| pH | 6.8–7.0 Acceptable pH range 6.5–7.5 | |

Osm = 350–360 mOsm/kg

The preconditioning of the suspension of red blood cells in the diluent preferably is accomplished at 22° C. to 27° C. for a time period of 48 hours. This short period of two days of preconditioning is a marked improvement over prior art, which required in vitro red blood cells to be treated 15 to 21 days to achieve size and distribution width stabilization. If our preconditioning diluent is employed at lower than ambient temperature, more than two days will be needed, with time and temperature being inversely related. After preconditioning, the suspension can be stored at 4° C. to 6° C. until ready to be mixed with the media of this invention. At such time the preconditioned red blood cells are expressed from the diluent, as by centrifuging, and mixed with the media. The amount of red blood cells added to the media depends upon the desired cell count parameter required for the reference control.

The preconditioning diluent has two additional attributes: it increases the speed of sedimentation of the red cells during free standing and centrifuging; and it develops, at the interface between the diluent (supernatant) and the packed red cells, a mat-like grouping of the white blood cells and platelets of the whole blood. Hence, these attributes increase the ease of separating the red cells from the remainder of the whole blood constituents and eliminates need for repeated "washing" of the red cells to isolate them. Prior art separating techniques and diluents have need for repeated washings, which are traumatic to the red cell and cause some hemolysis, that is highly undesirable. Also, substantial losses of red cells are incurred during removal of the undesired whole blood components. As a consequence, prior art separating has had to compromise between completeness and trauma.

The components of the preconditioning diluent primarily responsible for providing the just discussed attributes are the lactose and the non-ionic surfactant; preferably Pluronic F68 manufactured by Wyandotte Chemicals Corporation, Wyandotte, Michigan. Lactose, a polyhydric carbohydrate, appears to cause some polarization of white blood cell and platelet cell wall components into polar and non-polar regions. Pluronic F68 is a polyoxypropylene chain (hydrophobic) with polyoxyethylene (hydrophilic) groups on the ends. As such, it exhibits both hydrophobic (non-polar) and hydrophilic (polar) properties. Apparently, this property enables the Pluronic F68 to be attracted to corresponding areas of the lactose-modified cell walls causing some adhesion. This action produces the "matting" characteristic by the white blood cells and platelets and also enhances the sedimentation of the red blood cells.

The new improved media of this invention contains lactose, one or more fungicides and antibiotics, or mixtures thereof, and also supplementary agents including purine nucleotides or nucleosides such as 5'-AMP, adenine and inosine. It also includes additional components not previously used in whole blood controls which alter red blood cell membranes. These new ingredients are (1) bile salts and cholic acid derivatives, (2) phenothiazine compounds and the salts thereof having antihistamine properties, and (3) 4-aminobenzoic acid ester derivatives and the salts thereof having local anesthetic properties. These components not only confer longer term stability to the media, but also make it substantially free from particulate matter especially in the lower particle size thresholds.

Although natural bile contains a number of substances, the compounds of special interest for this invention are the bile salts which are amides of cholic acid in which glycine or taurine is joined to the steroid acid by a peptide linkage, yielding respectively, glycocholic acid and taurocholic acid. Cholic acid, and dehydrocholic acid derived from cholic acid by oxidation, are also useful.

Phenothiazine compounds having antihistamine properties include the following compounds and the pharmaceutically active salts thereof, including the hydrochloride, tartrate, and the like. Examples of these compounds include phenothiazines which have the official or generic name of Methdilazine HCl, Trimeprazine tartrate, Promethazine HCl (phenergan), and Pyrathiazine HCl. These compounds are sold under numerous trade names. The basic structure of the phenothiazine compounds is:

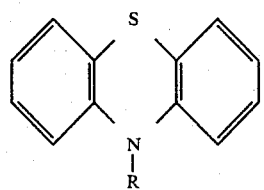

in which the substituent R is a substituted aminoalkyl or pyrrolidinylalkyl group.

Local anesthetic compounds useful for this invention include certain 4-aminobenzoic acid esters, and derivatives thereof having the structures $RHN-C_6H_4-COOR'$ or $RHN-C_6H_4-COOCH_2CH_2R'$ where R is hydrogen and lower alkyl, and R' is lower alkyl, dialkylaminoalkyl and dialkylamino. Examples of such compounds include Benzocaine, Procaine, Butacaine, Tetracaine, and Butethamine. An especially preferred compound is Procaine. The compounds are useful as the base or as a salt thereof, for example, the hydrochloride, butyrate, nitrate or borate.

Choice of the particular addition agent, or mixtures of agents, and the concentration is related particularly to solubility in the media.

Without being limited to any theory of action, the following description of the characteristics of red blood cells and action of the above described substances on the membrane of red blood cells gives some indication of the nature of the improved results brought about by their presence.

One advantage of using red blood cells instead of artificial surrogates in the control is that they are readily available in a physiologically reproducible condition, easily isolated by centrifugation, and easily resuspended in various test solutions. Water passes into and out of the cell very rapidly, in fact more than a hundred times as fast as any solute, so that osmotic equilibrium is maintained at all times. This causes the erythrocyte to act as an osmometer, proportionately increasing in size as solutes enter, and shrinking as they leave, so that a measurement of the size of the cell can be used to determine its content of a given solute. Because of its biconcave discoidal shape, however, moderate changes in volume are not accompanied by changes in the surface area of the membrane. Changes in volume beyond a certain point, on the other hand, result in hemolysis, a process in which the membrane becomes porous and allows the contents of the cell to diffuse into the surrounding medium.

Another advantage of the erythrocyte is its relative simplicity. It contains no nucleus, vacuoles, mitochrondria, vesicles, granules, etc., normally found in other cells. This is advantageous, since the cell forms a two-compartment system in which the membrane alone (with no cell wall) separates the internal and external media.

Erthrocytes constitute the major cells in blood. However, the erythrocytes themselves are an extremely heterogeneous group of cells. During their life span (120 days in man), they undergo structural and dimensional changes that can be associated with the loss of lipid, in addition to losing their biosynthetic ability. Young cells contain appreciably more lipid than older cells, which seem to have lost cholesterol and, predominantly, phospholipid in the aging process.

Normal erythrocytes develop membranes which are resistant to osmotic lysis when incubated in serum from patients with obstructive jaundice. Associated with this in vitro change in membrane surface area is a proportional increase in the membrane content of cholesterol, but not of phospholipid. Two factors, both related to serum bile acids, are perhaps responsible. Most important, bile acids cause a shift of free cholesterol from serum lipoproteins to the cell membranes. Bile acids also inhibit lecithin: cholesterol acyltransferase (LCAT) and alter the partition of free cholesterol within the red cell-serum pool, causing red cells to gain cholesterol and increasing the membrane surface area and the resistance to osmotic lysis.

The cholesterol content of the red cell membrane is not fixed in amount but can vary within wide limits of proportional changes in membrane surface area. Red cells that have become nonosmotically fragile have lost surface area. The rapid reversal of this process prevents the destruction of red cells depleted of cholesterol in vitro. The increase in cholesterol content and a small increase in phospholipid content, causes red cells to gain cholesterol. This leads to a reversible extension of cell surface area, which does not impair cell viability.

Purine nucleosides or nucleotides such as adenosine, inosine and 5'-AMP are important to the function of the red cell. Amino acid transport requires sodium transport, and the necessary component for sodium transport is 5'-AMP which increases sodium permeability of the red blood cell membrane. Adenosine triphosphate is necessary for restoring membrane deformability at near normal values. Regeneration of ATP, by incubation with adenosine, inosine, and 5'-AMP at room temperature (22° C.–27° C.) relates to preservation of membrane deformability.

Marked ATP depletion of stored red cells, or cells incubated in vitro, is accompanied by the disc to sphere shape transformation, a marked loss of membrane deformability, a loss of cell filterability, an increase in viscosity of packed cell suspensions and membrane associated hemoglobin and nonhemoglobin protein. Regeneration of ATP, by incubation with adenosine, produces significant reversal of all these changes.

The reversible loss of red cell deformability correlates with in vitro post transfusion survival of stored blood. Changes in deformability prior to shape change, plus observations that red cell ghosts in a media manifest the deformability properties of the intact cells from which they were prepared, suggest that intrinsic changes in the membrane are more critical determinants of deformability than shape alone. Stability of the red blood cells is further accomplished by certain 4-aminobenzoic acid ester derivations having local anesthetic action, such as procaine hydrochloride, and some phenothiazine compounds having antihistamine properties such as phenergan hydrochloride.

Growth of microorganisms is of primary concern in furnishing a stable whole blood reference control. Therefore, it is necessary to prescribe specific antibiotics to avoid contamination. Antibiotics with low solubility cause precipitation of small particulate matter, and result in a low level of activity against specific micro-organisms such as yeast and fungus.

The Coulter Counter ® Model S Plus, which counts platelets, as well as other electronic counting devices cannot tolerate the high background counts contributed by excess debris of any nature. The improved solubility of the antibiotics and fungicides in the preferred formulation provides a stabilizating media free of particulate matter that may produce erroneous results. Such results would perhaps endanger the diagnostic interpretation by the clinician. The stabilizing media also provides a more uniform whole blood reference control which closely simulates fresh whole blood, therefore, producing results that assure good quality control measures for all electronic devices.

The media of this invention can be employed with fresh whole blood red cells, (i.e. 2 days), aged red blood cells and/or expired red blood cells, which are preconditioned by the preconditioning diluent above described, and thus prepared for use in a whole blood reference control.

| Stabilizing Media for Conferring Long Term Stability on Red Blood Cells-Preferred Formulation, Approximate Amounts: Liter Formulation | | |
|---|---|---|
| 1 | Distilled water | 500. ml |
| 2 | Propyl paraben | 0.3–1.0 gm |
| 3 | Methyl paraben | 0.5–1.0 gm |
| 4 | Procaine hydrochloride | 0.1–0.5 gm |
| 5 | Deoxycholic acid | 0.1–0.9 gm |
| 6 | Lactose | 10.0–50.0 gm |
| 7 | Actidione | 0.1–0.6 gm |
| 8 | Trisodium citrate dihydrate | 3.0–8.0 gm |
| 9 | Citric acid monohydrate | 0.3–0.9 gm |
| 10 | Sodium dihydrogen phosphate monohydrate | 0.8–2.5 gm |
| 11 | Phenergan hydrochloride | 0.1–1.0 gm |
| 12 | Colistimethate, sodium | 0.2–0.9 gm |
| 13 | Penicillin G, sodium | $0.5 \times 10^6$–$3 \times 10^6$ units |
| 14 | Kanamycin sulfate | 0.2–0.8 gm |
| 15 | Neomycin sulfate | 0.2–1.0 gm |
| 16 | 5'-AMP | 0.4–1.0 gm |
| 17 | Adenine | 0.2–0.8 gm |
| 18 | Inosine | 0.4–1.0 gm |
| 19 | Dihydrostreptomycin sulfate | 0.2–1.0 gm |
| 20 | Tetracycline hydrochloride | 0.2–1.0 gm |
| 21 | 35% Bovine albumin | 100–350 ml |
| 22 | q.s. to 1 liter with distilled water | |

Since many of the chemicals listed above are known commercially by several names, the name given is a common name listed in the Merck Index, Ninth Edition (1976), published by Merck and Co., Inc., Rahway, N.J.

For best results the above ingredients #1 to #20 are added to distilled water in the order listed, allowing each ingredient to dissolve completely before the next ingredient is added. The product is then stirred at about 800 to 1200 RPM for 12 to 18 hours at 20° C. to 30° C. Then components #21 and #22 are added. The final product should have a pH in the range of 6.0 to 7.0 and an adjusted osmolality of 340±5 mOsm/kg; however, the osmolality could be within the range of 280 to 380 mOsm/kg. The product is filtered as needed, and stored at 4° C. to 6° C. The shelf life is about six months.

While certain representative embodiments and details have been shown for the purpose of illustrating the invention, it will be apparent to those skilled in the art that various changes and modifications may be made therein without departing from the spirit or scope of the invention.

What we claim and seek to be protected by United States Letters Patent is:

1. In a media for preparing whole blood hematology reference controls on addition of red blood cells thereto for devices using electronic means,
   said media being an aqueous solution of lactose, compatible bacteriostatic and fungicidal agents, and albumen, and being osmotically balanced at a preselected and controlled pH,
   the improvement which comprises including in a total amount sufficient to act as a cell membrane stabilizer, but insufficient to cause lysing of said red blood cells, at least one ingredient selected from the following groups:
   A. Bile salts and cholic acid derivatives; and
   B. Phenothiazine compounds having antihistamine properties,
   said controls having stability of at least 60 days for size distribution parameters, normal appearance of cells with respect to size and shape, and freedom from any particulate matter which causes erroneous results.

2. The media of claim 1 including at least one purine nucleotide or nucleoside.

3. The media of claim 1 including at least one purine nucleotide or nucleoside selected from the group consisting of
   5'-AMP
   adenine, and
   inosine.

4. The media of claim 1 in which said fungicide is selected from the group consisting of
   methyl paraben,
   ethyl paraben,
   propyl paraben,
   actidione and mixtures thereof.

5. The media of claim 1 including the antibiotic kanamycin sulfate.

6. In the media of claim 1 the improvement wherein said cholic acid derivative is deoxycholic acid.

7. The media of claim 1 including a phenothiazone salt having antihistamine properties.

8. The media of claim 1 including buffers to maintain a pH in the range of 6.0 to 7.5.

9. The media of claim 1 adjusted to an osmolality in the range of 280 to 380 milliosmoles.

10. In the media of claim 1, the further improvement wherein a 4-aminobenzoic acid ester derivative is added as an additional ingredient.

11. In the media of claim 1, the improvement wherein said antihistamine is phenergan.

12. In the media of claim 1, the improvement wherein said cholic acid derivative is deoxycholic acid in the amount of 0.1 to 0.9 gm. per liter formulation.

13. In the media of claim 1, the improvement wherein said antihistamine is phenergan in the amount of 0.1 to 1.0 gm. per liter formulation.

14. In a media for preparing whole blood hematology reference controls on addition of red blood cells thereto for devices using electronic means,
    said media being an aqueous solution of lactose, compatible bacteriostatic and fungicidal agents, and albumen, and being osmotically balanced at a preselected and controlled pH,
    the improvement which comprises including in a total amount sufficient to act as a cell membrane stabilizer, but insufficient to cause lysing of said red blood cells, a combination of deoxycholic acid and procaine hydrochloride,
    said controls having stability of at least 60 days for size distribution parameters, normal appearance of cells with respect to size and shape, and freedom from any particulate matter which causes erroneous results.

* * * * *